United States Patent [19]
Venturelli

[11] Patent Number: 5,971,990
[45] Date of Patent: Oct. 26, 1999

[54] SYSTEM FOR INTRODUCING AND POSITIONING EXPANDABLE STENTS

[75] Inventor: Andrea Venturelli, Concesio, Italy

[73] Assignee: INVATEC S.r.l., Concesio, Italy

[21] Appl. No.: 09/063,154

[22] Filed: Apr. 20, 1998

[51] Int. Cl.[6] .................................................. A61F 11/00
[52] U.S. Cl. .......................................................... 606/108
[58] Field of Search ................................ 606/108, 194, 606/195

[56] References Cited

U.S. PATENT DOCUMENTS

| | | | |
|---|---|---|---|
| 4,762,128 | 8/1988 | Rosenbluth | 606/192 |
| 5,026,377 | 6/1991 | Burton et al. | 606/108 |
| 5,779,731 | 7/1998 | Leavitt | 606/194 |
| 5,846,246 | 12/1998 | Dirks et al. | 606/108 |

*Primary Examiner*—Michael Buiz
*Assistant Examiner*—Vy Q Bui
*Attorney, Agent, or Firm*—McGlew and Tuttle, P.C.

[57] ABSTRACT

A catheter structure is provided for dilating and for positioning stents. The catheter structure includes a catheter having an inflatable balloon. Two collars are fixed around a catheter part inside the balloon and intended to define two annular shoulders one in front of the other and spaced apart in parallel. A tubular adapter is arranged around the catheter portion between the collar. The balloon, when empty, is wrapped around the collars with the tubular adapter comprised between same. The shoulders form bilateral axial closing means for a stent that is arranged and contracted around the empty and wrapped balloon.

13 Claims, 2 Drawing Sheets

SYSTEM FOR INTRODUCING AND POSITIONING EXPANDABLE STENTS

FIELD OF THE INVENTION

The present invention pertains to the instruments for the introduction and the positioning of mechanically dilating stent in the ducts or lumina of a live, either human or animal body.

BACKGROUND OF THE INVENTION

Stents are tubular molds which are made of biocompatible materials and are contracted on their introduction and then dilate for their stable insertion into the desired duct or lumen. Some types of stents dilate mechanically, and for their insertion they require the use of an expandable element arranged along the introducing instrument and acting inside the stent.

As the instrument for the introduction of mechanically dilating stents, a catheter having an inflatable balloon at its distal end of the type already used may also be used, e.g., for dilating arterial ducts or other lumina in a live body. Therefore, for the introduction operation, the balloon, empty, is wrapped tightly around a corresponding zone of the catheter, and the stent, in its turn, is arranged tightly around the balloon in order to remain fixed there during the introduction into a lumen.

In general then, the catheter, at the balloon, has a radiopaque marker in order to be able to control the position of the catheter and, therefore, that of the balloon in the duct or lumen in question.

However the requirements of a catheter for the simple dilation of ducts or lumina most often are incompatible with those of a catheter for the positioning of a stent, which is why specific catheters would be needed for one or the other operation.

A dilating catheter, for example, for angioplasty procedures, or the like, must have a small diameter, a low coefficient of surface friction, and a highly resistant balloon. On the other hand, a catheter for the positioning of stents must have a remarkable friction, at least at the balloon, be made of a material having a surface that is adapted to the interior of the closed, i.e., contracted stent, and have a diameter of the balloon, when closed, i.e., wrapped around the catheter, that is at least slightly greater than the internal diameter of the closed stent. All this is to hold the stent and to prevent its loss during the insertion in a duct or lumen.

Otherwise, a diameter in the zone of the catheter, including the closed balloon wrapped there, that is smaller than the internal diameter of the closed stent that is applied there may cause:

- a so-called overlapping resulting from a corrugation and an overlapping of some parts of the stent with possible deformation of its structure, if the stent is contracted too tightly in order to adhere to such a zone; or
- an improper fixing of the stent with the possibility of losing it during the introduction if the stent, although suitably and correctly closed, does not adhere to the too-small outer surface of the catheter plus closed balloon.

SUMMARY AND OBJECTS OF THE INVENTION

Starting from these representative premises of the state of the art, the primary object of the present invention is to provide a valid solution to the problems mentioned above and to correspondingly provide an improved catheter structure, which is reliable for a correct arrangement of the stent contracted around the closed balloon and which makes it possible to reduce, if not to eliminate, the possibilities of release and loss of the stent during the phase of introduction into the duct or lumen in which it is inserted.

Another object of the present invention is to propose a catheter structure that can be used advantageously either as a catheter for dilating or a catheter for positioning expandable stents.

According to the invention, a catheter structure is provided for dilating and for positioning stents. The catheter structure includes a catheter having an inflatable balloon. Two collars are fixed around a catheter part inside the balloon and intended to define two annular shoulders one in front of the other and spaced apart in parallel. A tubular adapter is arranged around the catheter portion between the collar. The balloon, when empty, is wrapped around the collars with the tubular adapter comprised between same. The shoulders form bilateral axial closing or limiting means for a stent that is arranged and contracted around the empty and wrapped balloon.

In practice, the contracted stent is thus arranged and is held positively between the two shoulders, prevented from sliding axially and thus from being lost, and this is independent of the actual diameter of the catheter, of the material with which the balloon is made and of the degree of friction offered by the said balloon.

In addition, the diameter of the catheter portion between shoulders may be adapted by increasing it with the application of a tubular adapter.

Greater details of the present invention, as well as its other aspects and advantages, shall become more evident from the description below with reference to the attached drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
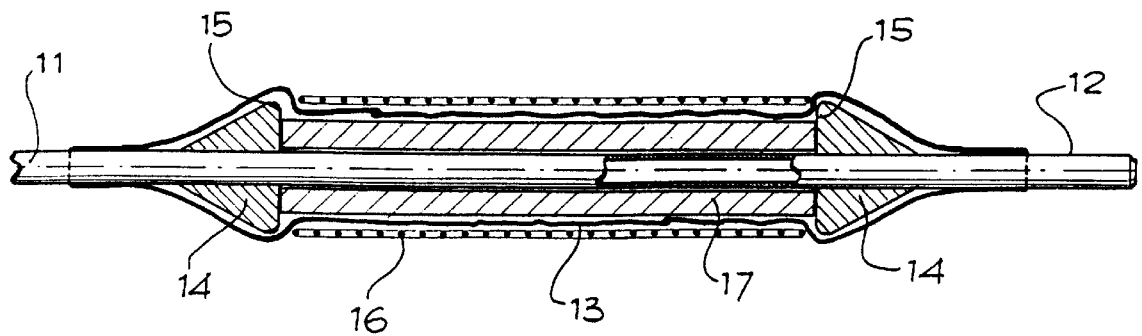
FIG. 1 is a partial sectional view of a catheter according to the present invention with wrapped balloon and stent contracted around the balloon between two conical collars.

Referring to the drawings in particular, a catheter generally designated 11 has, in a manner known per se, an inflatable balloon 13 on its distal section 12.

Two collars 14 are spaced apart and delimit two annular shoulders 15, one in front of the other, around the catheter. The two collars 14 are applied on the catheter part that is within the balloon.

Figure 2:
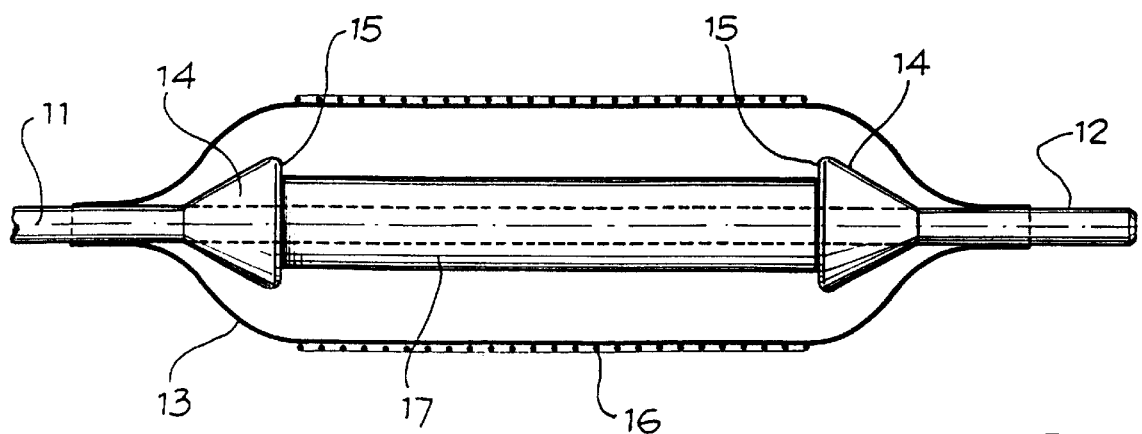
FIG. 2 is a similar view of the catheter of FIG. 1, but with the balloon inflated and the stent dilated.
Figure 3:
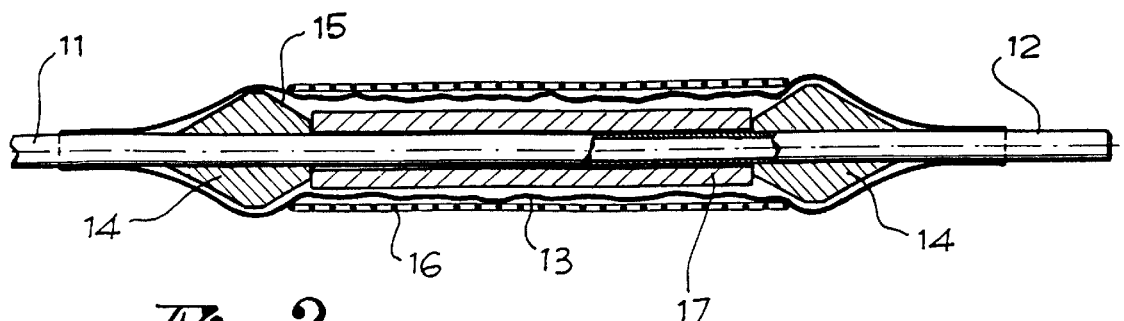
FIG. 3 is a partial sectional view showing part of a catheter with biconical collars.
Figure 4:
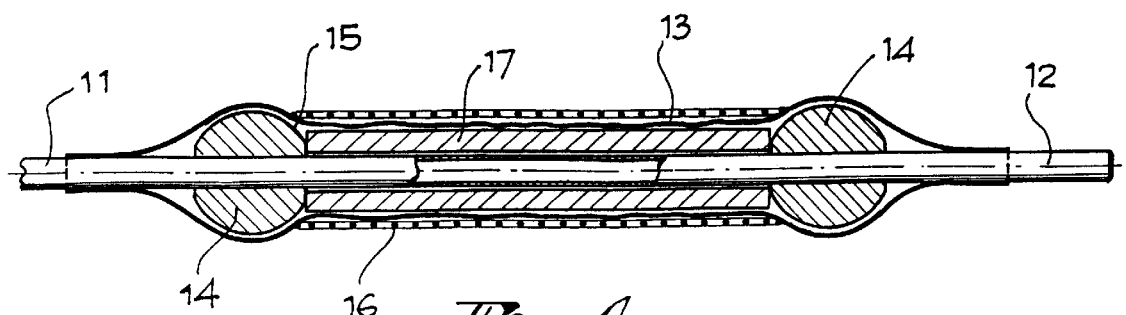
FIG. 4 is a view that is similar to that of FIG. 1, but in which the collars are defined by spherical elements.
Figure 5:
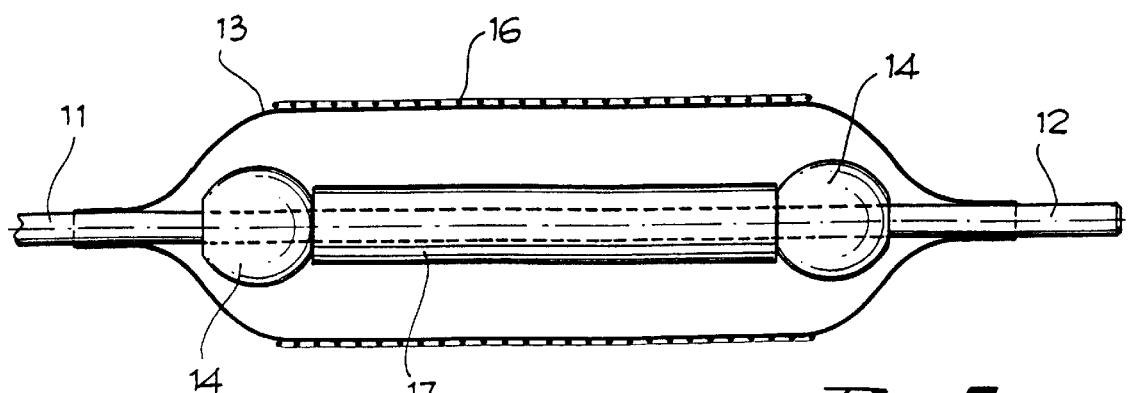
FIG. 5 is a view that is similar to that of FIG. 2, but in which the collars are defined by spherical elements.

The two collars 14 may preferably be conical, with opposite conicities, as shown in FIGS. 1 and 2, one towards the distal end 12 of the catheter and the other in the opposite direction, in order to facilitate the introduction and the extraction of the catheter in a duct or lumen of a body. As an alternative, the collars 14 may be biconical as shown in FIG. 3, or spherical as shown in FIGS. 4 and 5.

The collars 14 may be made of a radiopaque material in order to form markers which make it possible to find the position of the catheter in the duct or lumen, in which it is inserted.

The distance between the two collars and, therefore, between the annular shoulders 15 is at least slightly greater than the length of a stent 16 to be used and to be inserted with the dilating catheter described.

Therefore, to use this catheter in the positioning of an expandable stent 16, the empty balloon is wrapped tightly on the collars 14 and around the part of the catheter comprised between said collars. The stent 16 is then placed and contracted around the balloon and is held in the space comprised between the two annular shoulders 15 defined by the collars 14 as shown in FIGS. 1, 2 and 4.

If the catheter plus the balloon wrapped thereon has a suitable diameter, the contracted stent is adapted to the outer surface of the closed balloon with no overlapping and, moreover, positively held axially between the shoulders 15 and radially within the peripheral outline of the collars.

In the case of a particularly thin catheter, as in the catheters used for angioplasty, and in which the external diameter of the catheter plus the empty balloon wrapped thereon may be much smaller than the internal diameter of the contracted, i.e., closed, stent, without overlapping around the catheter part comprised between the two collars 14, a tubular adapter 17 held between the two shoulders 15 may be applied and so as to artificially increase the diameter of the catheter as shown in the drawings. Therefore, even in this case, the stent may be applied correctly on the catheter without the possibility of loss during the introduction into the duct or lumen in question.

FIGS. 2 and 5 of the drawings illustrate the condition of expansion of the balloon and of dilation of the stent for the release of same at the time of its insertion.

While specific embodiments of the invention have been shown and described in detail to illustrate the application of the principles of the invention, it will be understood that the invention may be embodied otherwise without departing from such principles.

What is claimed is:

1. A catheter structure for dilating and for positioning stents, comprising:
    a catheter part having a catheter diameter;
    an inflatable balloon associated with said catheter part;
    two collars fixed around said catheter part inside said balloon and defining two annular shoulders one in front of the other and spaced apart a distance, said shoulders defining shoulder surfaces, which are substantially in parallel;
    a tubular adapter arranged around a catheter portion of said catheter between said shoulder surfaces of said collars, said balloon, when empty, being wrapped around said collars with said tubular adapter disposed between said collars;
    a stent disposed outwardly of said balloon, disposed outwardly of said tubular adapter and disposed outwardly of said catheter, said stent being disposed between said shoulder surfaces, said shoulders forming bilateral axial limiting means for said stent that is arranged and contracted around the said empty and wrapped balloon.

2. The catheter structure in accordance with claim 1, wherein said collars are conical with opposite conicities, one towards a distal end of said catheter part and the other extending in an opposite direction.

3. The catheter structure in accordance with claim 1, wherein said collars are each biconical.

4. The catheter structure in accordance with claim 1 wherein said collars are spherical.

5. The catheter structure in accordance with the claim 2 wherein said collars are made of a radiopaque material.

6. The catheter structure in accordance with claim 1, wherein said tubular adapter is held between said shoulders and is intended to increase the external diameter of said catheter.

7. The catheter structure in accordance with the claim 3 wherein said collars are made of a radiopaque material.

8. The catheter structure in accordance with the claim 4 wherein said collars are made of a radiopaque material.

9. The catheter structure in accordance with the claim 1, wherein:
    said stent in a contracted state is adapted to the outer surface of the empty balloon with no overlapping and said stent is positively held axially between said shoulder surfaces and is disposed radially within a peripheral outline of the collars; and
    said tubular adapter is held between said two shoulder surfaces and provides a diameter which is greater than the diameter of said catheter.

10. A catheter and stent structure, comprising:
    a catheter having a substantially constant catheter diameter;
    an annular collar fixed to said catheter, said annular collar defining a shoulder with a shoulder surface;
    another annular collar fixed to said catheter, said another annular collar defining another annular collar shoulder, said shoulders being one in front of the other and spaced apart a distance, said shoulders defining shoulder surfaces, which are facing each other and are in parallel, each collar having a reduced diameter portion, one portion on a side of the collar extending towards a distal end of said catheter part and the other portion extending in an opposite direction;
    a tubular adapter arranged around a portion of said catheter between said shoulder surfaces of said collars, said adapter having an adapter diameter, which is greater than the diameter of said catheter, said tubular adapter being held between said two shoulder surfaces;
    an inflatable balloon, when empty, said balloon being wrapped around said collars and around said tubular adapter;
    a stent disposed outwardly of said balloon, disposed outwardly of said tubular adapter and outwardly of said catheter, said stent being disposed between said shoulder surfaces, said shoulders forming bilateral axial limiting means for said stent that is arranged and contracted around the said empty and wrapped balloon, said stent, in a contracted state, being adapted to the outer surface of the closed balloon with no overlapping of ends of said balloon and said stent being positively held axially between said shoulder surfaces and being disposed radially within a peripheral outline of the collars.

11. The catheter structure in accordance with claim 10, wherein said collars are each biconical.

12. The catheter structure in accordance with the claim 10 wherein said collars are made of a radiopaque material.

13. The catheter structure in accordance with claim 10, wherein said collars are conical with opposite conicities, one towards a distal end of said catheter part and the other extending in an opposite direction.

* * * * *